(12) United States Patent
Altshuler

(10) Patent No.: US 6,277,063 B1
(45) Date of Patent: *Aug. 21, 2001

(54) TRANSFERRING DEVICE FOR PENILE CONSTRICTOR

(76) Inventor: Yakov Altshuler, 66 Overlook Ter. #2E, New York, NY (US) 10001

( * ) Notice: Subject to any disclaimer, the term of this patent is extended or adjusted under 35 U.S.C. 154(b) by 0 days.

This patent is subject to a terminal disclaimer.

(21) Appl. No.: 09/552,510

(22) Filed: Apr. 19, 2000

Related U.S. Application Data

(63) Continuation-in-part of application No. 09/210,463, filed on Dec. 12, 1998.

(51) Int. Cl.[7] .................................................. A61F 5/00
(52) U.S. Cl. ................................................................ 600/39
(58) Field of Search .......................................... 600/38–41

(56) References Cited

U.S. PATENT DOCUMENTS

| | | | |
|---|---|---|---|
| 5,115,800 | * | 5/1992 | Matejevic et al. ...................... 600/38 |
| 5,125,890 | * | 6/1992 | Merrill et al. .......................... 600/39 |
| 5,195,943 | * | 3/1993 | Chaney ................................... 600/39 |
| 5,468,211 | * | 11/1995 | Welch .................................... 600/41 |
| 5,647,837 | * | 7/1997 | McCarty ................................ 600/38 |
| 5,997,470 | * | 12/1999 | Coates ................................... 600/38 |
| 6,036,635 | * | 3/2000 | Altshuler ............................... 600/41 |

* cited by examiner

Primary Examiner—John P. Lacyk
Assistant Examiner—Joseph A. Cadugan

(57) ABSTRACT

Transferring devices provided by the invention substantially improve efficacy of vacuum erection systems. Added to the system, the transferring device enables to dislodge one, two or more constrictors instantly. The external transferring device for penile constrictor comprises a pulling loop 4 attached to a mounting tube 22. An embodiment with the mounting tube inserted into the vacuum chamber (internal transferring device) is designated for vacuum chambers with abdominal air tight seal and for chambers with removably placed penile seal. An embodiment with a mounting tube 22 placed over the vacuum chamber 12 (external transferring device) is designated for vacuum erection systems with permanently inserted penile seal 14. Proposed transferring device can be easy retrofitted by the user into the existing system, without the need for special tools or skills. A method for transferring penile constrictors from the vacuum chamber onto erect penis has been proposed.

17 Claims, 3 Drawing Sheets

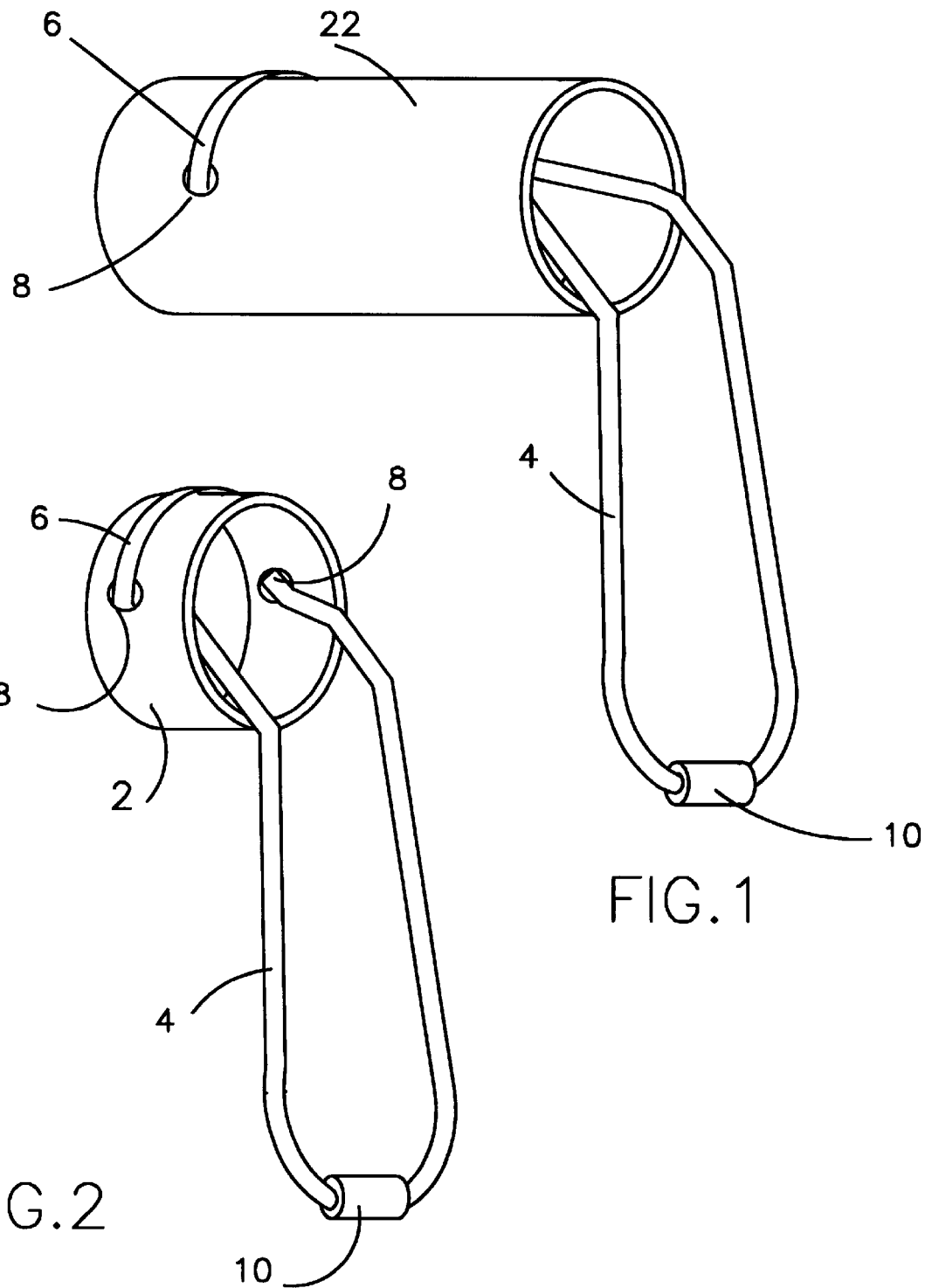

TRANSFERRING DEVICE FOR PENILE CONSTRICTOR

CROSS-REFERENCE TO RELATED APPLICATION

This is a continuation-in-part of Ser. No. 09/210,463 "Adjustable Penile Constrictor", filing date Dec. 12, 1998, Notice of Allowance Mar. 13, 2000.

BACKGROUND

1. Field of Invention.

The invention relates to vacuum erection devices for erectile dysfunction treatment and augmenting male potency, particularly to devices and methods for transferring penile constrictors.

2. Description of Prior Art.

Vacuum erection therapy is recognized by National Institute of Health as the first line remedy, preferable to other treatments of erection dysfunction-sex therapy, self injections, venous and arterial surgery, implantation of a penile prosthesis. It provides firm erection in the shortest time, without need of sexual arousal and faster than pills like Viagra, which could take another hour to work. It has a much higher success rate than pills, is safe, and it has no serious side effects.

Presently manufactured vacuum constriction devices comprise a vacuum chamber with an open end serving as an entrance, a closed end connected to a vacuum pump through a hose, and constriction rings placed on the vacuum chamber close to its open end. To achieve an erection the penis is inserted into the open end of the vacuum chamber, which is pressed to abdomen to provide an airtight seal. Then the vacuum is generated in the chamber with the manually or electrically operated vacuum pump. The partial vacuum inside the chamber causes blood flow into the penis, thus producing an erection. To sustain the erection, the constriction ring preinstalled on the vacuum chamber is forced to slip off onto the root of the penis. Being placed on the root of the penis, the constriction ring inhibits the blood flow from the penis thus sustaining erection. After this, the vacuum is released, and the chamber is removed from the erect penis.

Commercially available vacuum erection systems still have a number of drawbacks.

By now about 1.5 million of vacuum erection devices have been sold. Tens of thousands are being manufactured every year. To improve efficacy of devices—already sold and new ones—a new design concepts has to be implemented for improvements of the systems and elimination of their drawbacks.

Among drawbacks of available vacuum erection systems, the most often mentioned are: cumbersomeness, technical difficulties, painfulness, and lack of concealment. These drawbacks do not stem from vacuum erection concept. The concept is excellent as it allows the user to bypass numerous natural obstacles on a complicated way from initial desire to fill erection.

The drawbacks are resulting from design features of particular systems, assemblies and parts which form the system.

The goal of this invention is an improvement in a very important function of a vacuum erection system—transferring of a penile constrictor from the vacuum chamber onto the root of erect penis.

Quick and reliable dislodging of the constrictor is extremely important for successful vacuum erection treatment. The shortest delay between initial move of constrictor and complete constriction can cause penetration of air into the chamber and make erection weaker.

The user's guides for available vacuum erection devices instruct to push the constrictor ring with the finger towards the edge of the vacuum chamber to force it to slip. It is not always easy.

Men whose pubic tissue is not firm because of obesity or some other causes are often encountering problem of sucking soft pubic tissue into the chamber and covering proximal end of the chamber by overhanging abdomen and pubic tissue insomuch as 3–4 cm. Getting with the finger to the constrictor in this situation could be difficult and painful, a vacuum could be broken and erection lost.

A majority of users have to load two or more constrictor rings to provide pressure sufficient to hinder blood flow from the penis.

It is more difficult to transfer two or more rings instantly so that firmness is not lost during transfer—when the first ring constricts the base of the penis, air tightness can be damaged.

Different approaches for solving transfer problems are known in a prior art.

U.S. Pat. No. 4,753,227 "Erection Device and Method" of Jun. 28, 1988 to Rudolph Yanuck discloses a sleeve 46 which is axially slidable along the vacuum chamber for forcing constrictor to slip off This force is very substantial. During loading, the constrictor with the diameter of opening about 2 cm has to be extended to diameter about 7 cm (the outside diameter of the chamber). This is so difficult that many users cannot do it without special applicator. The inward radial pressure of the constrictor is very difficult to overcome by applying longitudinally directed force, especially if the user has to load two or more constriction rings.

The transferring device of this invention is an integral part of the system. It is not retrofittable by the users into another systems.

U.S. Pat. No. 5,115,800 "Apparatus for Achieving and Maintaining Penis Erection" of May 26, 1992 to Matejevic et al. discloses a transferring assembly with a double lever which pushes the bushing with its two projections. The bushing has a head which pushes the constrictor until it slips from the tube onto the base of the penis.

The system is mechanically complicated and it is not retrofittable by the users into existing systems.

In the U.S. Pat. No. 5,125,890 "Vacuum-Constriction Erection and Device" of Jun. 30, 1992 to Merrill et al. dislodging is performed by a flexible strap, adhesively attached to a rubber diaphragm near the open end of the vacuum chamber. During an upward movement of the strap it pushes the constrictor placed over tubular segment of the diaphragm towards the edge of the chamber and pulls the plug which releases the vacuum.

Drawbacks of this approach stem from the requirement of a very strong grip of the diaphragm to the chamber—it has to withstand shifting force of at least two dislodging constrictors. Placement of the diaphragm with such strong grip requires special tooling and skill, hardly available to users. The pivoting point (axe) of the strap can be provided only at the certain distance from the edge to make space for adhesive. Because of this, the constrictor cannot be brought beyond the chamber's edge by the upward movement of the strap during transfer. Besides, dislodging force is quite substantial, which makes adhesive attachment vulnerable to tearing.

U.S. Pat. No. 5,195,943 "Male Organ Restrictor Ring Applicator" of Mar. 23, 1993 to John Chaney discloses a sleeve contiguous with the constrictor. The sleeve is provided with a camming surface that reacts against a fixed cam element on the cylinder. When the sleeve is rotated, it is cammed axially towards the end of the cylinder and forces the constrictor to slip off. The drawbacks of this approach are following:.

1. Twisting motions for rotating the sleeve causes rocking of the chamber at the base of the penis which may affect air tightness and make erection weak. 2. The system is mechanically complicated and not retrofittable into existing devices by the users.

U.S. Pat. No. 5,213,563 "Apparatus for Obtaining an Artificial Erection" of May 25, 1993 to Allan Cox discloses a transfer ring, sidably installed on a cylindrical vacuum chamber and serving for forcing the constrictor to slip off by applying the force in the axial direction.

Difficulties of this approach were discussed above (R. Yanuck).

U.S. Pat. No. 5,997,470 "Penile Tube and Constrictor Ring Removal Guide System " of Dec. 7, 1999 to Frank Coates discloses a transferring device for a cylindrical vacuum chamber in two embodiments: one with the sleeve having axial movement and one with the sleeve having threaded rotational motion. The device with axial motion is not effective, especially when two or more constrictors have to be dislodged simultaneously.

The device with the threaded sleeve is mechanically complicated. Both embodiments are integrated with specific systems and are not suitable for retrofitting into existing devices by individual users.

Discussed prior art does not show simple and effective solutions for transferring devices. It does not show a transferring device with rigid mounting tube and a pulling loop easily attachable to existing vacuum chambers.

U.S. Pat. No. 6,036,635 "Erection Control System" of Mar. 14, 2000 to Yakov Altshuler discloses transferring device insertable into a vacuum chamber for simultaneous dislodging of a penile seal and a constriction device loaded over the outside surface of the vacuum chamber.

Patent application Ser. No. 09/210,463, Notice of Allowance of Mar. 13, 2000 to Yakov Altshuler "Adjustable Penile Constrictor" discloses a mounting tube for penile rigidity device for sustaining naturally obtained erection (i.e. without the use of a vacuum erection device).

The goal of this invention is to provide simple and reliable transferring devices for existing vacuum chambers with abdominal seal and for chambers with retrofittable penile seals, recited in a patent application Ser. No. 09/543,274 of Yakov Altshuler, filed Apr. 5, 2000. The use of the devices should be simple and intuitive. The devices should be retrofittable, so that the users who bought vacuum erection devices years ago would be able to install new transferring devices and successfully use them without special tools or help from outside.

SUMMARY OF THE INVENTION

Accordingly, the invention provides simple and effective transferring devices, easy retrofittable to existing vacuum erection systems. Proposed transferring devices easy dislodge one, two or more constrictors by applying force to pulling loop with a finger. The invention provides:

1. Two embodiments of an internal transferring device:
   a) having a retaining tube with two holes for retaining a pulling loop;
   b) having a tubular shell and a retaining ring for attachment of a pulling loop The internal transferring devices are designated for systems with abdominal seal and for systems with removably placed penile seal.

2. External transferring device, placed over the vacuum chamber and designated for vacuum erection systems with internal penile seal, proposed in patent application Ser. No. 09/543,274 of Apr. 4, 2000 of Y. Altshuler.

BRIEF DESCRIPTION OF THE DRAWINGS

FIG. 1—external transferring device with a mounting tube, pulling loop, handle;

FIG. 2—internal transferring device with a retaining tube;

Figure 3:
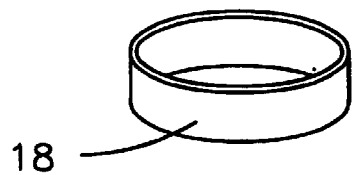
FIG. 3—retaining ring.

REFERENCE NUMERALS IN DRAWINGS 2 retaining tube
4 pulling loop
6 pulling loop's retaining segment
8 holes
10 handle
12 vacuum chamber
14 internal penile seal
16 constrictor
18 retaining ring
20 tubular shell with internal rim
22 mounting tube for external transfering device
24 internal rim

INTERNAL TRANSFERRING DEVICES

The embodiments are designated for vacuum erection devices with abdominal air tight seal and for vacuum erection devices with external penile seal removably placed over the vacuum chamber.

Internal Transferring Device with a Retaining Tube and a Pulling Loop

Figure 7:
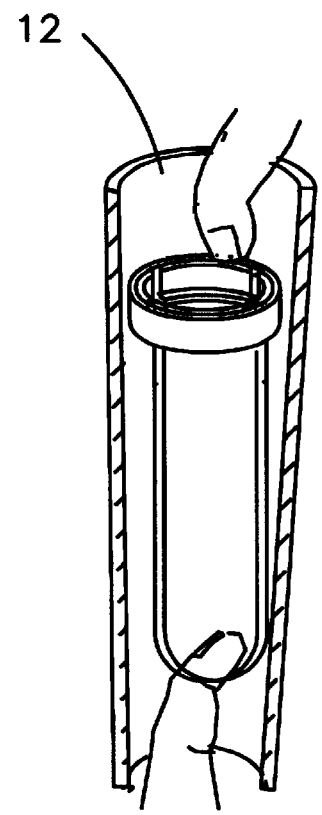
FIG. 7—placement of an internal transferring device into the vacuum chamber.
Figure 8:
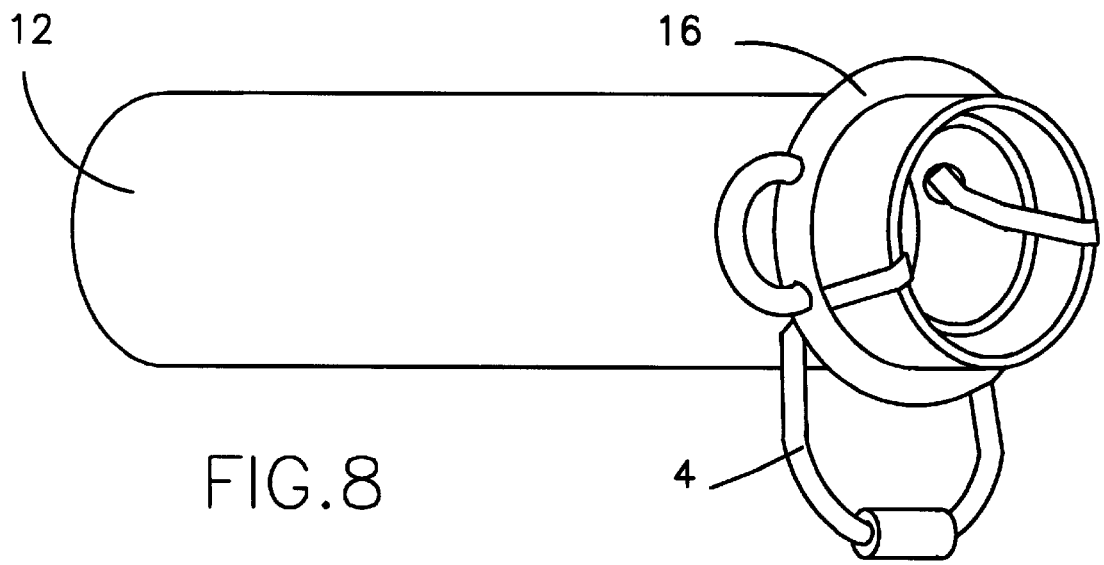
FIG. 8—vacuum chamber, internal transferring device with a retaining tube, and constrictor.

FIG. 2 shows an internal transferring device, consisting of a retaining tube 2 and a pulling loop 4. The loop is attached to the retaining tube through the holes 8 so that the retaining segment 6 of the pulling loop is arcuately adjacent to the outside surface of the retaining tube between the holes 8. The ends of the loop are tied with a knot covered by a segment of the latex tubing, forming a handle 10. The pulling loop 4 is made of a textile strip about 0.3–0.4 cm. wide with the length of about 20 cm. The retaining tube with the pulling loop is coaxially installed into the vacuum chamber (FIG. 7), so that the outside surface of the retaining tube fits the inside surface of the vacuum chamber. The retaining tube with the pulling loop tightly fit into the open end of the vacuum chamber (FIG. 8).

Internal Transferring Device with a Tubular Shell, a Retaining Ring and a Pulling Loop The embodiment comprises a tubular shell 20 with an internal rim 24 (FIG. 4), retaining ring 18 (FIG. 3), and a pulling loop 4. The loop is wrapped around the retaining ring 18 (FIG. 5). The ring 18 is inserted and pressed into the tubular shell 20, so that the loop 4 is squeezed between the inside surface of the tubular shell 20 and the outside surface of the retaining ring 18. (FIG. 6). Such arrangement enhances loop's attachment, as it is pressed to the rim 24 by retaining ring 8.

Figure 4:
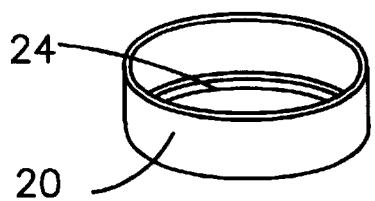
FIG. 4—tubular shell with an internal rim.
Figure 5:
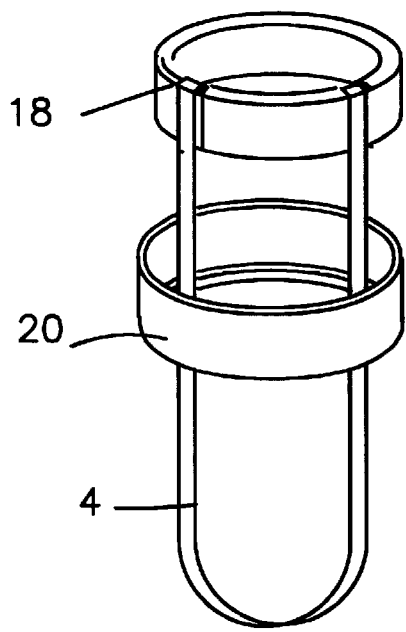
FIG. 5—assembling of a tubular shell, a retaining ring and a pulling loop.
Figure 6:
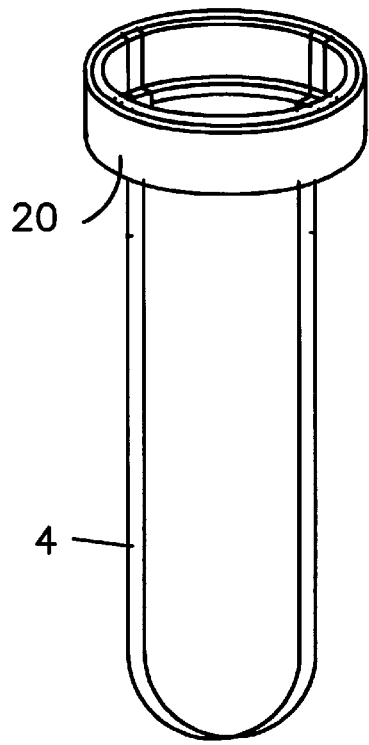
FIG. 6—assembled internal transferring device with a tubular shell and a retaining ring.

Assembling of this embodiment of the transferring device is performed as it is shown in FIGS. 3–5, with following steps: 1. Wrapping the ends of the loop 4 around the retaining ring 18 in axial direction around the ends of generatrix of the retaining ring, with angular distance between wrapped ends about 120 degree. 2. Inserting of retaining ring 18 with the wrapped loop's ends into the tubular shell 20, pulling the loop and firmly pressing the retaining ring until it stops. The assembled internal transferring device of this embodiment is shown in FIG. 6. If there is a need for changing the pulling loop 4, detachment of the retaining ring 18 from the tubular shell 20 is performed by pulling the loop 4 in the opposite direction.

The majority of existing vacuum chambers have smaller diameter at the entrance (the open end) and larger at the distal end. To install the transferring device, the user inserts the tubular shell with the pulling loop into the wider end of the chamber and pushes the tube towards the entrance, then catches the loop and pulls it until the tubular shell stops. (FIG. 7). From this permanent position, the tubular shell can be removed by pressing it towards the distal end of the vacuum chamber.

Operation of the Embodiments

Figure 9:
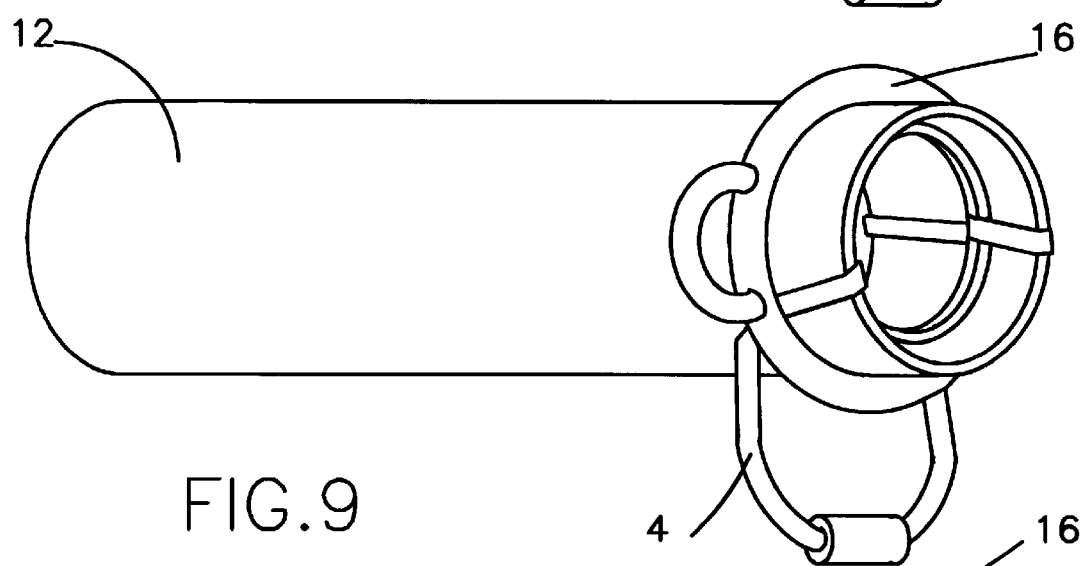
FIG. 9—vacuum chamber, internal transferring device with a tubular shell, retaining ring, and constrictor.

Prior to placement of the constricting device, the hanging part of the pulling loop 4 is tightened along the outside surface of the vacuum chamber and stretched towards its distal end. Then the constrictor 16 is loaded so that it presses the pulling loop to the vacuum chamber and the segment of the loop with a handle hangs behind the constrictor (FIGS. 8,9). After applying vacuum and achieving erection, the penile constrictor 16 has to be transferred onto the erect penis. The user applies his finger to the loop and pulls it towards the perineum, which forces the constrictor to slip off.

EXTERNAL TRANSFERRING DEVICE

FIG. 1 shows an external transferring device for mounting over the vacuum chamber. The device consists of a mounting tube 22 and a pulling loop 4. The inside wall of the mounting tube conforms to the shape of the outside surface of the proximal end of the vacuum chamber. The length of the tube is about 6 cm, the wall thickness is about 0.15 cm. The loop is attached to the mounting tube through the holes 8 so that the middle retaining segment 6 of the pulling loop is arcuately adjacent to the outside surface of the mounting tube between the holes 8. The pulling loop 4 is made of a textile strip about 0.3–0.4 cm. wide with the length of about 20 cm.

The vacuum chamber has to be coaxially installed into the mounting tube 22 with the pulling loop 4 so that the inside surface of the mounting tube 22 fits the outside surface of the vacuum chamber 12. The pulling loop is squeezed between the outside surface of the vacuum chamber 12 and the inside surface of the mounting tube 22.

To install the transferring device, the user inserts the open proximal end of the chamber 12 into the open end of the mounting tube and pushes the tube towards the chamber.

Operation of the Embodiment

Figure 10:
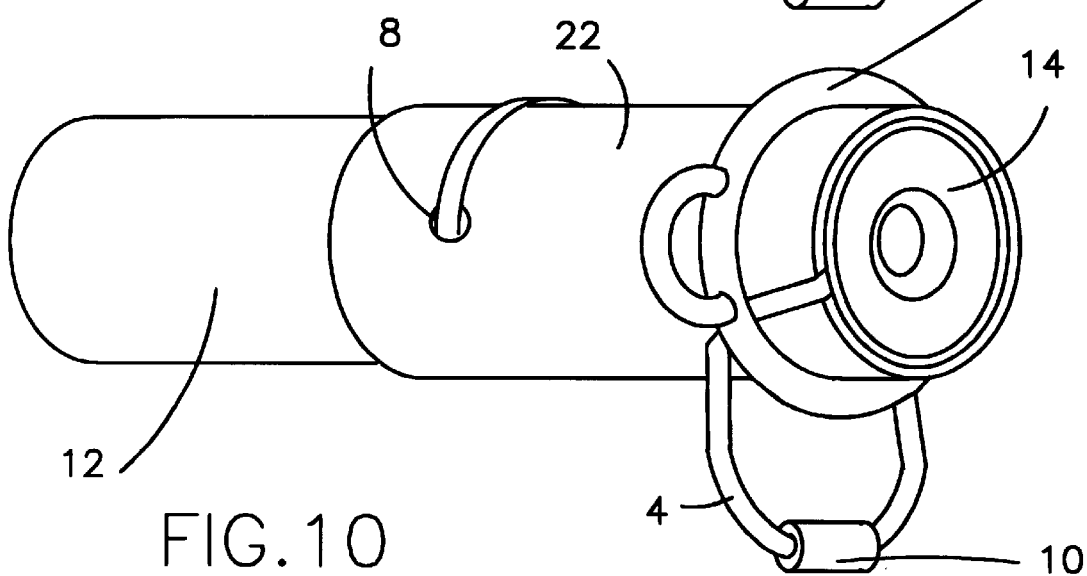
FIG. 10—vacuum chamber, external transferring device with a mounting tube, and constrictor.

Prior to placement of the constricting device, the pulling loop 4 is stretched along the outside surface of the mounting tube towards the distal end of the vacuum chamber . Then the constrictor 16 is loaded so that it presses the pulling loop to the mounting tube and the segment of the loop hangs behind the constrictor. (FIG. 10). After achieving erection, the user applies his finger to the loop and pulls it towards the perineum. This forces the constrictor to slip off from the mounting tube onto erect penis.

Although the description above contains many specifics, these should not be construed as limiting the scope of the invention but as merely providing illustrations of some of the presently preferred embodiments of this invention. Many other variations are possible with the device still remaining simple and economical.

Accordingly, the scope of the invention should be determined not by the embodiments illustrated, but by the appended claims and their legal equivalents.

What is claimed is:

1. An externally placed transferring device for dislodging a penile constrictor attached to a vacuum chamber, said chamber having inside and outside surfaces, proximal and distal ends and adapted to receive a penis, comprising:

a) an external mounting tube of rigid material having inside size sufficient for inserting and firmly holding said proximal end of said vacuum chamber and adapted for placement of said constrictor on a proximal end of said mounting tube, b) a pulling loop attached to said external mounting tube and adapted for forcing said constrictor to slip from said external mounting tube onto erect penis for sustaining erection.

2. The externally placed transferring device for penile constrictor according to claim 1 wherein said mounting tube has a length about 6 cm and a wall thickness about 0.15 cm.

3. The externally placed transfering device for penile constrictor according to claim 1 wherein said pulling loop is formed from a flexible strip with a length from an end to an end about 20 cm and a width about 0.3–0.4 cm.

4. The externally placed transferring device for penile constrictor according to claim 1 wherein said mounting tube has holes through which said ends of said flexible strip are led to form an arcuate retaining segment for holding said pulling loop adjacent to said outside surface of said mounting tube with further connection of said ends to each other, whereby said pulling loop is formed.

5. The externally placed transferring device for penile constrictor according to claim 1, wherein said pulling loop having a first arcuate portion adjacent to said outside surface of said mounting tube, a second portion sandwiched between said inside surface of said mounting tube and said outside surface of said vacuum chamber, a third portion extended along said outside surface of said mounting tube and pressed by said constrictor, and a forth portion hanging beyond said constrictor and adapted for forcing said constrictor to slip from said mounting tube onto erect penis.

6. A method for transferring penile constrictor from a vacuum chamber with a rigid mounting tube with a pulling loop attached externally over the proximal end of said vacuum chamber, comprising steps:

a) stretching said pulling loop along an outside surface of said mounting tube, b) loading said constrictor over said mounting tube so that said pulling loop is pressed by said constrictor to said mounting tube and a segment of said pulling loop is hanging beyond said constrictor, c) inserting a penis into said vacuum chamber and creating erection, d) pulling said hanging segment of said pulling loop towards the perineum of the penis, whereby said constrictor slips from said mounting tube onto erect penis.

7. An internally placed transferring device for dislodging a penile constrictor from a vacuum chamber, said vacuum chamber having inside and outside surfaces, proximal and distal ends and adapted to receive a penis, comprising:
   a) a retaining tube of rigid material having outside diameter slightly smaller then the inside diameter of said vacuum chamber for inserting and finally holding said retaining tube in said proximal end of said vacuum chamber;
   b) a pulling loop attached to said retaining tube and adapted for forcing said constrictor to slip from said proximal end of said vacuum chamber onto erect penis for sustaining erection.

8. The internally placed transferring device for penile constrictor according to claim 1 wherein said retaining tube has a length about 1 cm and a wall thickness about 0.15 cm.

9. The internally placed transferring device for penile constrictor according to claim 1 wherein said pulling loop is formed from a flexible strip with a length from an end to an end about 20 cm and a width about 0.4 cm.

10. The internally placed transferring device for penile constrictor according to claim 1 wherein said retaining tube has holes through which said ends of said flexible strip are led to from an arcuate retaining segment for holding said arcuate segment of said pulling loop adjacent to said outside surface of said retaining tube with further connection of said ends to each other, whereby said pulling loop is formed.

11. The internally places transfering device for penile constrictor according to claim 7, wherein said pulling loop having a first arcuate portion sandwiched between said outside surface of said retaining tube and said inside surface of said vacuum chamber, a second portion adjacent to said inside surface of said retaining tube, the third portion extended along said outside surface of said vacuum chamber and pressed by said constrictor, and a forth portion hanging beyond said constrictor and adapted for forcing said constrictor to slip from said vacuum chamber onto erect penis.

12. A method for transferring penile constrictor from a vacuum chamber having a rigid retaining tube with a pulling loop inserted into a proximal end of said vacuum chamber, comprising steps:
   a) stretching said pulling loop along an outside surface of said retaining tube,
   b) loading said constrictor over said pulling loop so that said pulling loop is pressed by said constrictor to said vacuum chamber and a hanging segment of said pulling loop is formed beyond said constrictor,
   c) inserting a penis into said vacuum chamber and creating erection,
   d) pulling said hanging segment of said pulling loop towards the perineum of the penis, whereby said constrictor slips from said vacuum chamber onto erect penis.

13. An internally placed transferring device for dislodging a penile constrictor from a vacuum chamber, said chamber having an inside and an outside surfaces, proximal and distal ends and adapted to receive a penis, comprising:
   a) a tubular shell for assembling said internally placed transferring device, having proximal and distal ends, outside and inside surfaces and an internal rim in said proximal end of said tubular shell;
   b) a retaining ring of rigid material having outside diameter slightly smaller then the diameter of said inside surface of said tubular shell and an inside diameter approximately the same as the inside diameter of said internal rim;
   c) a pulling loop attached to said retaining ring and adapted for forcing said constrictor to slip from said proximal end of said vacuum chamber onto erect penis for sustaining erection.

14. The internally ,placed transferring device for penile constrictor according to claim 13 wherein said retaining ring has a length about 1 cm and a wall thickness about 0.15 cm.

15. The internally placed transferring device for penile constrictor according to claim 13 wherein said tubular shell has a length about 1.5 cm and a wall thickness about 0.15 cm.

16. The internally placed transferring device for penile constrictor according to claim 13 wherein said pulling loop is formed from a flexible strip with a length from an end to an end about 20 cm and a width about 0.4 cm., each end of said strip being wrapped in the axial direction around two generatrix of said retaining ring at angular distance about 120 degree.

17. The internally placed transfering device for penile constrictor according to claim 13 wherein said retaining ring with said pulling loop is pressed into said tubular shell, whereby said wrapped ends of said pulling loop are squeezed between said outside surface of said retaining ring and said inside surface of said tubular shell.

* * * * *